US009821028B2

(12) United States Patent
Cook et al.

(10) Patent No.: US 9,821,028 B2
(45) Date of Patent: *Nov. 21, 2017

(54) METHODS OF CONTROLLING PARASITIC WORMS IN ANIMALS

(71) Applicant: WISCONSIN ALUMNI RESEARCH FOUNDATION, Madison, WI (US)

(72) Inventors: Mark Eric Cook, Madison, WI (US); Daniel Meilahn Schaefer, Madison, WI (US); Mitchell Raymond Schaefer, Taopi, MN (US); Jordan Marshall Sand, Madison, WI (US); Larry Smith, Lodi, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/329,439

(22) Filed: Jul. 11, 2014

(65) Prior Publication Data

US 2016/0008436 A1    Jan. 14, 2016

(51) Int. Cl.
*A61K 38/20* (2006.01)
*C07K 16/24* (2006.01)
*A61K 39/00* (2006.01)

(52) U.S. Cl.
CPC ........ *A61K 38/2066* (2013.01); *C07K 16/244* (2013.01); *A61K 2039/505* (2013.01); *C07K 2317/11* (2013.01); *C07K 2317/23* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 5,102,872 A | 4/1992 | Singh et al. | |
| 5,741,489 A | 4/1998 | Pimentel | |
| 5,989,867 A | 11/1999 | Knappe et al. | |
| 6,608,172 B1 | 8/2003 | Chiou | |
| 7,867,480 B1* | 1/2011 | Cevc et al. | 424/85.1 |
| 8,652,457 B2 | 2/2014 | Sand et al. | |
| 2006/0228448 A1 | 10/2006 | Bolleau et al. | |
| 2009/0022691 A1 | 1/2009 | Moore et al. | |
| 2009/0186038 A1 | 7/2009 | Reed | |
| 2013/0109619 A1 | 5/2013 | Tarasova et al. | |
| 2014/0017248 A1* | 1/2014 | Sand et al. | 424/139.1 |
| 2014/0127220 A1 | 5/2014 | Sand et al. | |
| 2015/0037277 A1 | 2/2015 | Cook et al. | |

FOREIGN PATENT DOCUMENTS

| | | | | |
|---|---|---|---|---|
| AU | WO 9404174 A1 * | 3/1994 | | A61K 39/0003 |
| WO | 9506657 A1 | 3/1995 | | |
| WO | 2008086621 A1 | 7/2008 | | |
| WO | 2015017132 A1 | 2/2015 | | |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Brown et al. (J Immunol. May 1996;156(9):3285-91 at 3290.*
Vajdos et al. (J Mol Biol. Jul. 5, 2002;320(2):415-28 at 416).*
Fawzi et al (Clinical and Vaccine Immunology Sep. 2013: 20:9; 1352-1359).*
Alba-Hurtado et al, "Immune Responses Associated with Resistance to Haemonchosis in Sheep," BioMed Research International, vol. 2013, Article ID 162158, 11 pages, 2013.*
Bai et al (PLoS Pathog 5(10):Oct. 2009).*
Cruse et al., Illustrated Dict. of Immunology, 2nd ed., CRC Press, 2003.*
Arai et al.; "Effects of In Vivo Administration of Anti-IL-10 Monoclonal Antibody on the Host Defence Mechanism Against Murine *Salmonella* Infection"; Immunology; 85; pp. 381-388; (1995).
Chen et al; "Oral Administration of a Combination of Select Lactic Acid Bacteria Strains to Reduce the *Salmonella* Invasion and Inflammation of Broiler Chicks"; Poultry Science; 91(9); pp. 2139-2147; (2012).
Ghebremicael et al.; "Associated of Interleukin-10 Cluster Genes and *Salmonella* Response in the Chicken"; Poultry Science; 87(1); pp. 22-26; (2008).
International Search Report and Written Opinion; International Application No. PCT/US2014/047002; Fling Date Jul. 17, 2014; dated Dec. 12, 2014; 14 pages.
Sand et al._"Oral Antibody to Interleukin-10 Prevents Growth Suppression by Coccidia Infection"; from Poultry Association 101st Annual Meeting Abstracts; Abstract P310; Jul. 9-12, 2012; Poult. Sci. 91(suppl.1) p. 107.
U.S. Appl. No. 13/957,601, filed Aug. 2, 2013; NonFinal Office Action dated May 7, 2015; 21 pages.
U.S. Appl. No. 13/957,601, filed Aug. 2, 2013; co-pending application, Methods of Reducing *Salmonella* in Poultry.
Alam et al.; "A2A Adenosine Receptor (AR) Activation Inhibits Pro-inflammatory Cytokine Production by Human CD4+ Helper T Cells and Regulates Helicobacter-induced Gastritis and Bacterial Persistence"; Mucosal Immunology; 2(3); pp. 232-242; (2009).
"Anthelmintic Resistance: An Examination of its Growing Prevalence in the U.S. Cattle Herd", Executive Summary of the 2005 Anthelmintic ResistanceRoundtable;http://www.merck-animal-health-usa.com/binaries/Anthel_Resist_Exec_Summary_2_tcm96-86774.pdf.
Barnes et al.; "Selection of Different Genotype Larvae and Adult Worms for Anthelmintic Resistance by Persistent Short-Acting Avermectin/Milbemycins"; International Journal for Parasitology; 31; pp. 720-727; (2001).

(Continued)

*Primary Examiner* — Brian J Gangle
*Assistant Examiner* — Andrea McCollum
(74) *Attorney, Agent, or Firm* — Cantor Colburn LLP

(57) ABSTRACT

Disclosed herein are methods of controlling parasitic worms in herbivorous mammals and other species by orally administering an isolated antibody that specifically binds the interleukin-10 peptide or an interleukin-10 peptide. In the case of herbivorous mammals such as cattle, for example, administration of the anti-IL-10 antibodies increases weight gain and increases feed efficiency in the animals.

40 Claims, 2 Drawing Sheets

(56) References Cited

OTHER PUBLICATIONS

Campbell et al.; "Susceptability to Cryptosporidium Parvum Infections in Cytokine- and Chemokine-Receptor Knockout Mice"; Journal of Parasitology; 88(5); pp. 1014-1016; (2002).
Canals, et al.; "Cytokine Profile Induced by a Primary Infection with Ostertagia Ostertagi in Cattle"; Veterinary Immunology and Immunopathology; 58; pp. 63-75; (1997).
Coles et al.; "The Detection of Anthelmintic Resistance in Nematodes of Veterinary Importance"; Veterinary Parasitology; 136; pp. 167-185; (2006).
Collier et al.; "Coccidia-induced Mucogenesis Promotes the Onset of Necrotic Enteritis by Supporting Clostridium Perfringens Growth"; Veterinary Immunology and Immunopathology; 112; pp. 104-115; (2008).
Cook, M. E.; "Triennial Growth Symposium: A Review of Science Leading to Host-Targeted Antibody Strategies for Preventing Growth Depression Due to Microbial Colonization"; J. Animal Sci; 89; pp. 1981-1990; (2011).
De Meulenaer et al.; "Isolation and Purification of Chicken Egg Yolk Immunoglobulins: A Review"; Food and Agricultural Immunology; 13(4); pp. 275-288; (2001).
Filho et al.; "Humoral and Cellular Immune Response Generated by Different Vaccine Programs Before and After *Salmonella enteritidis* Challenge in Chickens"; Vaccine; 30; pp. 7637-7643; (2012).
Lee et al.; "IL-10 Suppresses Bactericidal Response of Macrophages Against *Salmonella typhimurium*"; Journal of 49(6); pp. 1050-1053; (2011).
Li, Robert W. et al.; "Localized Complement Activation in the Development of Protective Immunity Against Ostertagia Ostertagi Infections in Cattle"; Veterinary Parasitology; 174; pp. 247-256; (2010).
Li, Robert W., et al.; "Local Inflammation as a Possible Mechanism of Resistance to Gastrointestinal Nematodes in Angus Heifers"; Veterinary Parasitology; 145; pp. 100-107 (2007).
Rothwell et al.; "Cloning and Characterization of Chicken IL-10 and Its Role in the Immune Response to Eimeria maxima"; Journal of Immunology; 173; pp. 2675-2682; (2004).
Setta et al.; "Early immune dynamics following Infection with *Salmonella enterica* serovars Enteridis, Infantis, Pullorum and Gallinarum: Cytokine and chemokine gene expression profile and cellulsr changes of chicken ceca tonsils"; Comparative Immunology, Microbiology and Infectious Diseases; 35; pp. 397-410; (2012).
Symonds et al.; "Bifidobacterium Infantis 35624 Protects Against *Salmonella*-Induced Reductions in Digestive Enzyme Activity in Mice by Attenuation of the Host Inflammatory Response"; Clinical and Translational Gastroenterology; 3, e15; doi:10.1038/ctg.2012.9; pp. 1-10; (published online May 10, 2012).
Wei et al.; "*Salmonella enterica* Serovar Typhi Plasmid Impairs Dendritic Cell Responses to Infection"; Curr Microbiol; 65; pp. 133-140; (2012).
Williams, R.B.; "Anticcoccidial Vaccines for Broiler Chickens: Pathways to Success"; Avian Pathology; 31(4); pp. 317-353; (2002).
Yazwinski et al.; "Fecal Egg Count Reduction and Control Trial Determinations of Anthelmintic Efficacies for Several Parasiticides Utilizing a Single Set of Naturally Infected Calves"; Veterinary Parasitology; 164; pp. 232-241; (2009).
Hartog et al.; "Modulation of Human Immune Responses by Bovine Interleukin-10"; PLoS One; 6(3); pp. 1-10; (2011).
Hodek et al.; "Chicken Antibodies—Superior Alternative for Conventional Immunoglobulins"; Proc. Indian Sci Acad; B69(4); pp. 461-468; (2003).
Bobeck, et al.; Oral Peptide Specific Egg Antibody to Intestinal Sodium-dependent Phosphate Co-transporter-2b is Effective at Altering Phosphate Transport in Vitro and in Vivo; Poultry Science; 94; pp. 1128-1137; (2015).
Jones & Martino et al.; "Targeted localized Use of Therapeutic Antibodies: A Review of Non-systemic, Topical and Oral Applications"; Biotechnology; 36(3); pp. 506-520; (2016).
Arendt et al.; "Interleukin-10 Neutralizing Antibody for Detection of Intestinal Luminal Levels and as a Dietary Additive in Eimeria Challenged Broiler Chicks"; Poultry Science; 95; pp. 430-438; (2016).
Bobeck et al.; "Oral Antibodies to Human Intestinal Alkaline Phosphatase Reduce Dietary Phytate Phosphate Bioavailability in the Presence of Dietary 1Alpha-hydroxycholecalciferol"; Poultry Science; 95; pp. 570-580; (2016).
Yadav et al.; "Gastrointestinal Stability of Therapeutic Anti-TNF Alpha IgG1 Monoclonal Antibodies"; International Journal of Pharmaceutics; 502; pp. 181-187; (2016).
Aly et al.; "Agreement Between Bovine Respiratory Disease Scoring Systems for Pre-weaned Dairy Calves"; Animal Health Research Reviews; 15(2); pp. 148-150; (2014).
Erova et al.; Protective Immunity Elicited by Oral Immunization of Mice with *Salmonella enterica* Serovar Typhimurium Braun Lipoprotein (LPP) and Acetyltransferase (MsbB); Front Cell Infect Microbiol; 6; 148; 14 pages; (2016) 10.3389/fcimb.2016.00148.
Greenspan et al.; "Defining Epitopes: It's Not As Easy as It Seems"; Nature Biotechnology; 7; pp. 936-937; (1999).
MacCallum et al.; "Antibody-antigen Interactions: Contact Analysis and Binding Site Topography"; J. Mol. Biol. 262; pp. 732-745; (1996).
Nuflor; "Bovine Respiratory Diseases: A New Look at Causes and Signs of Disease"; found in MERCK Animal Health ; http://www.nuflor.com/diseases/brd-nlac.asp; 4 pages; printed Mar. 3, 2017.
Paul, Fundamental Immunology, Third Edition (textbook), "Fv Structure and Diversity in Three Dimensions" pp. 292-295; Raven Press, New York (1993).
Salazar et al.; "Systemic *Salmonella* Infection Requires Interleukin 10 Production in Mice"; Front. Immunol. Conference Abstract:IMMUNOCOLOMBIA2015 at the 11th Congress of the Latin American Association of Immunology, 2015; doi: 10.3389/conf.fimmu.2015.05.00144.

* cited by examiner

SEQUENCE LISTING

<160> NUMBER OF SEQ ID NOS: 40

<210> SEQ ID NO 1
<211> LENGTH: 8
<212> TYPE: PRT
<213> ORGANISM: Gallus gallus

<400> SEQUENCE: 1

Asp Asp Glu Leu Asn Ile Gln Leu
1               5

<210> SEQ ID NO 2
<211> LENGTH: 8
<212> TYPE: PRT
<213> ORGANISM: Gallus gallus

<400> SEQUENCE: 2

Val Leu Pro Arg Ala Met Gln Thr
1               5

<210> SEQ ID NO 3
<211> LENGTH: 8
<212> TYPE: PRT
<213> ORGANISM: Meleagris gallopavo

<400> SEQUENCE: 3

Val Leu Pro Arg Ala Met Lys Thr
1               5

<210> SEQ ID NO 4
<211> LENGTH: 8
<212> TYPE: PRT
<213> ORGANISM: Gallus gallus

<400> SEQUENCE: 4

Glu Lys Met Asp Glu Asn Gly Ile
1               5

<210> SEQ ID NO 5
<211> LENGTH: 8
<212> TYPE: PRT
<213> ORGANISM: Gallus gallus

<400> SEQUENCE: 5

Glu Pro Thr Cys Leu His Phe Ser
1               5

<210> SEQ ID NO 6
<211> LENGTH: 7
<212> TYPE: PRT
<213> ORGANISM: Sus scrofa

<400> SEQUENCE: 6

Asp Gln Met Gly Asp Leu Leu
1               5

<210> SEQ ID NO 7
<211> LENGTH: 7
<212> TYPE: PRT
<213> ORGANISM: Bos taurus

<400> SEQUENCE: 7

Asp Gln Leu His Ser Leu Leu
1               5

```
<210> SEQ ID NO 8
<211> LENGTH: 8
<212> TYPE: PRT
<213> ORGANISM: Sus scrofa

<400> SEQUENCE: 8

Val Met Pro Lys Ala Glu Ser Asp
1               5

<210> SEQ ID NO 9
<211> LENGTH: 8
<212> TYPE: PRT
<213> ORGANISM: Bos taurus

<400> SEQUENCE: 9

Val Met Pro Gln Ala Glu Asn His
1               5

<210> SEQ ID NO 10
<211> LENGTH: 8
<212> TYPE: PRT
<213> ORGANISM: Sus scrofa

<400> SEQUENCE: 10

Ser Lys Leu Gln Glu Arg Gly Val
1               5

<210> SEQ ID NO 11
<211> LENGTH: 8
<212> TYPE: PRT
<213> ORGANISM: Bos taurus

<400> SEQUENCE: 11

Ser Glu Leu Gln Glu Arg Gly Val
1               5

<210> SEQ ID NO 12
<211> LENGTH: 8
<212> TYPE: PRT
<213> ORGANISM: Sus scrofa

<400> SEQUENCE: 12

Glu Asn Ser Cys Ile His Phe Pro
1               5

<210> SEQ ID NO 13
<211> LENGTH: 8
<212> TYPE: PRT
<213> ORGANISM: Bos taurus

<400> SEQUENCE: 13

Asp Ser Ser Cys Ile His Leu Pro
1               5

<210> SEQ ID NO 14
<211> LENGTH: 7
<212> TYPE: PRT
<213> ORGANISM: Ovis aries

<400> SEQUENCE: 14

Asp Gln Leu Asn Ser Met Leu
1               5
```

```
<210> SEQ ID NO 15
<211> LENGTH: 8
<212> TYPE: PRT
<213> ORGANISM: Ovis aries

<400> SEQUENCE: 15

Asn Met Leu Gln Glu Arg Gly Val
1               5

<210> SEQ ID NO 16
<211> LENGTH: 8
<212> TYPE: PRT
<213> ORGANISM: Ovis aries

<400> SEQUENCE: 16

Asp Ser Ser Cys Thr His Phe Pro
1               5

<210> SEQ ID NO 17
<211> LENGTH: 8
<212> TYPE: PRT
<213> ORGANISM: Equus caballus

<400> SEQUENCE: 17

Asp Gln Leu Asp Asn Met Leu Leu
1               5

<210> SEQ ID NO 18
<211> LENGTH: 8
<212> TYPE: PRT
<213> ORGANISM: Equus caballus

<400> SEQUENCE: 18

Val Met Pro Gln Ala Glu Asn His
1               5

<210> SEQ ID NO 19
<211> LENGTH: 8
<212> TYPE: PRT
<213> ORGANISM: Equus caballus

<400> SEQUENCE: 19

Ser Lys Leu Gln Glu Lys Gly Val
1               5

<210> SEQ ID NO 20
<211> LENGTH: 8
<212> TYPE: PRT
<213> ORGANISM: Equus caballus

<400> SEQUENCE: 20

Glu Asn Ser Cys Thr His Phe Pro
1               5

<210> SEQ ID NO 21
<211> LENGTH: 7
<212> TYPE: PRT
<213> ORGANISM: Gadus morhua

<400> SEQUENCE: 21

Asp Asp Leu Glu Ile Gly Leu
1               5
```

```
<210> SEQ ID NO 22
<211> LENGTH: 12
<212> TYPE: PRT
<213> ORGANISM: Gadus morhua

<400> SEQUENCE: 22

Val Leu Pro Thr Ala Ile Ala Asp Met Thr Glu Glu
1               5                   10

<210> SEQ ID NO 23
<211> LENGTH: 8
<212> TYPE: PRT
<213> ORGANISM: Gadus morhua

<400> SEQUENCE: 23

Thr Gln Met Glu Gly Lys Gly Pro
1               5

<210> SEQ ID NO 24
<211> LENGTH: 7
<212> TYPE: PRT
<213> ORGANISM: Gadus morhua

<400> SEQUENCE: 24

Asn Gln Cys Cys Arg Phe Val
1               5

<210> SEQ ID NO 25
<211> LENGTH: 8
<212> TYPE: PRT
<213> ORGANISM: Canis familiaris

<400> SEQUENCE: 25

Asp Lys Leu Asp Asn Ile Leu Leu
1               5

<210> SEQ ID NO 26
<211> LENGTH: 7
<212> TYPE: PRT
<213> ORGANISM: Canis familiaris

<400> SEQUENCE: 26

Val Met Pro Arg Ala Glu Asn
1               5

<210> SEQ ID NO 27
<211> LENGTH: 8
<212> TYPE: PRT
<213> ORGANISM: Canis familiaris

<400> SEQUENCE: 27

Ser Lys Leu Gln Glu Lys Gly Val
1               5

<210> SEQ ID NO 28
<211> LENGTH: 8
<212> TYPE: PRT
<213> ORGANISM: Canis familiaris

<400> SEQUENCE: 28

Glu Asp Asp Cys Thr His Phe Pro
1               5
```

```
<210> SEQ ID NO 29
<211> LENGTH: 8
<212> TYPE: PRT
<213> ORGANISM: Felis catus

<400> SEQUENCE: 29

Asp Glu Leu His Ser Ile Leu Leu
1               5

<210> SEQ ID NO 30
<211> LENGTH: 8
<212> TYPE: PRT
<213> ORGANISM: Felis catus

<400> SEQUENCE: 30

Val Met Pro Gln Ala Glu Asn Glu
1               5

<210> SEQ ID NO 31
<211> LENGTH: 8
<212> TYPE: PRT
<213> ORGANISM: Felis catus

<400> SEQUENCE: 31

Ser Lys Leu Gln Glu Lys Gly Val
1               5

<210> SEQ ID NO 32
<211> LENGTH: 8
<212> TYPE: PRT
<213> ORGANISM: Felis catus

<400> SEQUENCE: 32

Glu Asp Asn Cys Thr His Phe Ser
1               5

<210> SEQ ID NO 33
<211> LENGTH: 8
<212> TYPE: PRT
<213> ORGANISM: Lepus curpaeums

<400> SEQUENCE: 33

Asp Gln Leu Asn Ser Met Leu Leu
1               5

<210> SEQ ID NO 34
<211> LENGTH: 8
<212> TYPE: PRT
<213> ORGANISM: Lepus curpaeums

<400> SEQUENCE: 34

Val Met Pro Gln Ala Glu Asn His
1               5

<210> SEQ ID NO 35
<211> LENGTH: 8
<212> TYPE: PRT
<213> ORGANISM: Lepus curpaeums

<400> SEQUENCE: 35

Ser Lys Leu Gln Glu Glu Gly Val
1               5
```

```
<210> SEQ ID NO 36
<211> LENGTH: 8
<212> TYPE: PRT
<213> ORGANISM: Lepus curpaeums

<400> SEQUENCE: 36

Glu Asn Ser Cys Ile His Phe Pro
1               5

<210> SEQ ID NO 37
<211> LENGTH: 8
<212> TYPE: PRT
<213> ORGANISM: Cavia porcellus

<400> SEQUENCE: 37

Asp Gln Leu Asp Asn Val Leu Leu
1               5

<210> SEQ ID NO 38
<211> LENGTH: 8
<212> TYPE: PRT
<213> ORGANISM: Cavia porcellus

<400> SEQUENCE: 38

Val Met Pro Gln Ala Glu Lys His
1               5

<210> SEQ ID NO 39
<211> LENGTH: 8
<212> TYPE: PRT
<213> ORGANISM: Cavia porcellus

<400> SEQUENCE: 39

Asn Lys Leu Gln Asp Gln Gly Val
1               5

<210> SEQ ID NO 40
<211> LENGTH: 8
<212> TYPE: PRT
<213> ORGANISM: Cavia porcellus

<400> SEQUENCE: 40

Glu Asp Ser Cys Ala His Phe Pro
1               5
```

METHODS OF CONTROLLING PARASITIC WORMS IN ANIMALS

FIELD OF THE DISCLOSURE

The present disclosure is related to methods for killing and controlling worms (Helminths), and compositions for killing and controlling worms in animals, such as cattle.

BACKGROUND

The disease or group of diseases described generally as helminthiasis is due to infection of an animal host with parasitic worms known as helminths. Helminthiasis is a widespread and serious economic problem in livestock animals such as swine, sheep, horses, cattle, goats, and poultry. Helminthiasis is also a serious health risk to humans and companion animals such as dogs, cats and other pets.

Among the helminths, the group of worms described as nematodes causes widespread, and often times serious, infection in various species of animals. Several of the more common genera of nematodes infecting the digestive systems of the animals referred to above are *Ascaris, Haemonchus, Ostertagia, Oesophagostomum, Cooperia, Strongyloides*, and *Trichostrongylus*. Certain helminths, such as *Cooperia* and *Oesophagostomum*, attack primarily the intestinal tract, while others, such as *Haemonchus* and *Ostertagia* are more prevalent in the stomach. *Haemonchus* and *Ostertagia* sp. are costly parasites in the cattle, sheep and goat industries.

The adverse economic impacts on agriculture of the parasitic infections known as helminthiases are well known. Helminth infections interfere with animal digestion and nutrient absorption and thus cause anemia, malnutrition, weakness, and weight loss. Helminths can also cause severe damage to the walls of the gastrointestinal tract and other tissues and organs and, if left untreated, may result in death of the infected host animal. Accordingly, infected livestock will exhibit poor production performance as manifested by little or no weight gain, metabolic disturbances, reproductive abnormalities, and reduced milk production and quality.

Parasitic infections detract also from the quality of human and companion animal life. In addition, the impact on humans is particularly severe in third world nations. Helminthiasis causes similar symptoms in humans and companion animals to those found in livestock, including nausea, diarrhea, anemia, malnutrition, weight loss, weakness, and, in severe cases, death.

What is needed are improved methods for the treatment of helminthiases in animals such as livestock species.

BRIEF SUMMARY

In an aspect, a method of controlling parasitic worms having a lifecycle stage that includes the gastrointestinal tract of an herbivorous mammal comprises orally administering to the herbivorous mammal an effective amount of an interleukin-10 peptide or an isolated antibody that specifically binds an interleukin-10 peptide.

In another aspect, a method of providing resistance to reinfection with a parasitic worm having a lifecycle stage that includes the gastrointestinal tract of an herbivorous mammal comprises orally administering to the herbivorous mammal an effective amount of an interleukin-10 peptide or an isolated antibody that specifically binds an interleukin-10 peptide, wherein the herbivorous mammal is infected with the parasitic worm at the time of oral administration of the interleukin-10 peptide or the isolated antibody that specifically binds the interleukin-10 peptide.

In another aspect, a method of increasing weight gain or increasing feed efficiency in an herbivorous mammal comprises orally administering to the herbivorous mammal an effective amount of an interleukin-10 peptide or an isolated antibody that specifically binds an interleukin-10 peptide, wherein the herbivorous mammal is infected with or is suspected of being infected with a parasitic worm having a lifecycle stage that includes the gastrointestinal tract of the herbivorous mammal.

In yet another aspect, a method of controlling parasitic worms having a lifecycle stage that includes the gastrointestinal tract of a companion animal comprises orally administering to the companion animal an effective amount of an interleukin-10 peptide or an isolated antibody that specifically binds an interleukin-10 peptide. In one aspect, the method comprises determining that the companion animal is infected with the parasitic worm prior to administration of the interleukin-10 peptide or isolated antibody that specifically binds the interleukin-10 peptide.

In another aspect, a method of controlling parasitic worms having a lifecycle stage that includes the gastrointestinal tract of grazing poultry comprises orally administering to the grazing poultry an effective amount of an interleukin-10 peptide or an isolated antibody that specifically binds an interleukin-10 peptide.

Figure 1:
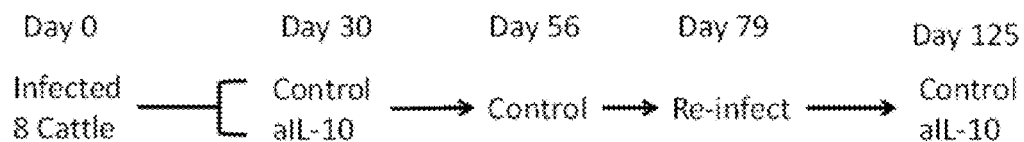
FIG. 1 shows the timeline of treatment of calves with anti-interleukin-10 (anti-IL-10) antibody, including initial infection and later reinfection.

The above-described and other features will be appreciated and understood by those skilled in the art from the following detailed description, drawings, and appended claims.

DETAILED DESCRIPTION

Described herein are methods of controlling parasitic worms having a lifecycle stage that includes the gastrointestinal tract of an animal, including for example, helminths. It was found that when an isolated antibody that specifically binds an IL-10 peptide was included in the feed of cattle exposed to parasitic worms, the cattle developed resistance to a subsequent challenge with a parasitic worm such as *Haemonchus* sp. Resistance in the cattle was indicated by an improvement in weight gain and reduced egg shedding compared to a control group of cattle fed a control diet with no antibody.

While the methods disclosed herein are illustrated for cattle, the methods can be generalized to all species that are susceptible to infection by parasitic worms having a lifecycle stage that includes the gastrointestinal tract. Specifically, because IL-10 is common to all animal species, albeit with some sequence variation, the present methods are applicable to a wide variety of animal species including herbivorous mammals and companion animals. In addition, while it was previously shown that anti-IL-10 antibodies are effective against protozoal infections in animals and *Salmonella* infections in poultry, parasitic worm(s) are completely different types of parasites in that they are multicellular eukaryotic organisms and are classified as animals, so it was not expected that anti-IL-10 antibodies would be effective against a completely different species of infectious agents. In addition, no currently available pharmaceutical therapies can control bacteria, protozoa and nematodes, thus the present findings were very unexpected.

In one aspect, a method of controlling parasitic worms having a lifecycle stage that includes the gastrointestinal tract of an herbivorous mammal comprises orally administering to the herbivorous mammal an effective amount of an interleukin-10 peptide or an isolated antibody that specifically binds an interleukin-10 peptide (an anti-IL-10 antibody). Orally administering the interleukin-10 peptide or anti-IL-10 antibody includes administering the peptide or antibody in a feed composition, for example.

Also included is a method of increasing weight gain or increasing feed efficiency in an herbivorous mammal, the method comprising orally administering to the herbivorous mammal an effective amount of an interleukin-10 peptide or an isolated antibody that specifically binds an interleukin-10 peptide. In specific aspects, the herbivorous mammal is infected with or is suspected of being infected with a parasitic worm having a lifecycle stage that includes the gastrointestinal tract of the herbivorous mammal. As used herein, the term infected also includes infested which generally means overrun with a large number of parasitic worms.

In specific aspects, the herbivorous mammal is suspected of infection with the parasitic worm having a lifecycle stage that includes the gastrointestinal tract of the herbivorous mammal. For example, the herbivorous mammal may be a member of a population that is infected with parasitic worms, or an animal that is grazed in an area that is known to harbor parasitic worms.

In certain aspects, the methods further comprise decreasing the mortality rate of the mammal.

In another aspect, a method of providing resistance to reinfection with a parasitic worm having a having a lifecycle stage that includes the gastrointestinal tract of an herbivorous mammal comprises orally administering to the herbivorous mammal an effective amount of an interleukin-10 peptide or an isolated antibody that specifically binds an interleukin-10 peptide, wherein the herbivorous mammal is infected with the parasitic worm at the time of oral administration of the interleukin-10 peptide or the isolated antibody that specifically binds the interleukin-10 peptide.

In certain aspects, the effective amount of the interleukin-10 peptide or the anti-IL-10 antibody is effective to increase weight gain in the herbivorous mammal, and/or the effective amount of the interleukin-10 peptide or the anti-IL-10 antibody is effective to reduce egg shedding in the herbivorous mammal, and/or the effective amount of the interleukin-10 peptide or the anti-IL-10 antibody is effective to reduce reinfection by parasitic worms in a population of herbivorous mammals. Effective amounts of an interleukin-10 peptide or anti-IL-10 antibody are 10 g/Kg feed to 0.001 mg/Kg feed, specifically 5 g/Kg feed to 0.1 g/Kg feed, and more specifically 1.2 g/Kg feed to 0.341 g/Kg feed.

As used herein, an herbivorous mammal is a mammal that feeds on pasture and/or forages and/or bedding for at least a portion of the year. Herbivory is practiced when any of these species grazes, consumes preserved forage, or ingests fibrous bedding materials. As used herein, herbivorous mammals include omnivorous mammals that can practice herbivory during at least a portion of their lifetime such as pigs. Animals that feed on pasture and forages or bedding contaminated with feces are particularly susceptible to infection by parasitic worms which often find their way into the gastrointestinal tract of the animal through contaminated food. Nearly all foraging mammals will be exposed to parasitic worms. As used herein, pasture includes land covered with grass or legumes that are suitable for ingestion by herbivores. Pasture forages include cool- and warm-season grass species as well as legumes, for example, clover and alfalfa. Herbivorous mammals include for example, ruminant and pre-ruminant mammals. In cattle, for example, the pre-ruminant phase is the first 2-3 weeks of life when the calf is feeding primarily on milk or milk replacer. Pre-ruminant animals have an undeveloped rumen which must undergo physiological and microbiological changes to accomplish digestion of high fiber feeds. The ruminant phase occurs when the calf is weaned and the rumen develops so that the animal can digest dry feeds.

Exemplary herbivorous mammals include bovine (cattle, water buffalo, bison, and yak), equine, ovine, caprine, llamas, alpacas, deer, elk, and pigs.

In an embodiment, the method further comprises determining if the herbivorous mammal, or a representative mammal of the population of herbivorous mammals, is infected with a parasitic worm. For example, feces can be examined for the presence of helminth eggs and nucleic acid-based techniques can further be used to identify the particular strain of helminth infecting the gastrointestinal tract of the animal.

In specific aspects, the herbivorous mammal is part of a population of mammals that are infected with parasitic worms that are resistant to antihelminthic agents. Wide-ranging resistance to current antihelminthic treatment results in reduced productivity and increased treatment costs, particularly in the cattle, sheep and goat industries. The advantage of the anti-IL-10 antibodies disclosed herein is that there does not appear to be a mechanism for the parasites to develop resistance to the antibodies. Thus, anti-IL-10 treatment as described herein will allow for natural vaccination of herbivorous animals with limited side-effects and reduced resistance. Antihelminthic agents include benzimidizoles (mebendazole, flubendazole, fenbendazole, oxfendazole, oxibendazole, albendazole, albendazole sulfoxide, thiabendazole, thiophanate, febantel, netobimin, and triclabendazole), hydropyrimidines (pyrantel, morantel, oxantel), imidazothiazoles (levamisole, tetramisole), or macrocylic lactones (avermectin, milbemycin).

In one aspect, the IL-10 peptide or anti-IL-10 antibody is orally administered to the herbivorous mammal daily for a period of 2 weeks or less, and then administration of the antibody is stopped for a period of time, such as for at least 2 weeks, at least 3 weeks, or longer. Without being held to theory, it is believed that daily administration for a 2 week period or less will provide sufficient immune protection from reinfection by parasitic worms for a period of 2-3 weeks or longer once administration of the antibody has ceased. In one aspect, after 2 weeks of daily administration, the administration of the isolated antibody that specifically binds the interleukin-10 peptide is not resumed for at least 2 weeks, at least 3 weeks, or longer.

In another aspect, a method of controlling parasitic worms having a lifecycle stage that includes the gastrointestinal tract of grazing poultry comprises orally administering to the grazing poultry an effective amount of an interleukin-10 peptide or an isolated antibody that specifically binds an interleukin-10 peptide. Pastured poultry grazing is an alternative to indoor confinement of poultry and can also be referred to as free-range poultry. Like grazing cattle, for example, grazing poultry are also exposed to parasitic worms. Thus, the methods disclosed herein are also particularly useful for the treatment of grazing poultry.

In another aspect, a method of providing resistance to reinfection with a parasitic worm having a having a lifecycle stage that includes the gastrointestinal tract of grazing poultry comprises orally administering to the grazing poultry an effective amount of an interleukin-10 peptide or an isolated antibody that specifically binds an interleukin-10 peptide, wherein the grazing poultry is infected with the parasitic worm at the time of oral administration of the interleukin-10 peptide or the isolated antibody that specifically binds the interleukin-10 peptide.

In certain aspects, the effective amount of the interleukin-10 peptide or the anti-IL-10 antibody is effective to increase weight gain in the grazing poultry, and/or the effective amount of the interleukin-10 peptide or the anti-IL-10 antibody is effective to reduce egg shedding in the herbivorous mammal, and/or the effective amount of the interleukin-10 peptide or the anti-IL-10 antibody is effective to reduce reinfection by parasitic worms in a population of herbivorous mammals. Effective amounts of an interleukin-10 peptide or anti-IL-10 antibody are 0.0001 mg/Kg feed to 10 g/Kg feed, specifically 0.01 g/Kg feed to 5 g/Kg feed, and more specifically 0.34 g/Kg feed to 1 g/Kg feed. In one embodiment, administering the effective amount of the interleukin-10 peptide or the isolated antibody that specifically binds the interleukin-10 peptide decreases the mortality rate of the grazing poultry.

In one aspect, the IL-10 peptide or anti-IL-10 antibody is orally administered to the grazing poultry daily for a period of 2 weeks or less, and then administration of the antibody is stopped for a period of time, such as for at least 2 weeks, at least 3 weeks, or longer. Without being held to theory, it is believed that daily administration for a 2 week period or less will provide sufficient immune protection from reinfection by parasitic worms for a period of 2-3 weeks or longer once administration of the antibody has ceased. In one aspect, after 2 weeks of daily administration, the administration of the isolated antibody that specifically binds the interleukin-10 peptide is not resumed for at least 2 weeks, at least 3 weeks, or longer.

In addition to herbivorous animals and poultry, companion animals such as dogs and cats can be infected with parasitic worms having a lifecycle stage that includes the gastrointestinal tract of the companion animal. Hookworm, for example, is a parasitic nematode that lives in the small intestine of its host, such as a dog or a cat. Infection with hookworm generally occurs when the host animal steps on the larvae, for example, by stepping on fecal matter. The larvae can penetrate the skin of the foot and, once inside the body, migrate through the vascular system to the lungs and then the trachea, at which point they are swallowed, passing down the digestive system to the intestine where the larvae mature into worms. Other parasitic worms that infect dogs and cats include roundworms, whipworms and tapeworms.

In an embodiment, a method of controlling parasitic worms having a lifecycle stage that includes the gastrointestinal tract of a companion animal comprises orally administering to the companion animal an effective amount of an interleukin-10 peptide or an isolated antibody that specifically binds an interleukin-10 peptide. In one aspect, the method further comprises determining that the companion animal is infected with the parasitic worm. Determining that the companion animal is infected with a parasitic worm can include analysis of a fecal sample for eggs such as performing a fecal floatation test, and also nucleic acid-based tools for diagnosis of infection and identification of the parasite.

As used herein, the term companion animal includes dogs, cats, rabbits, guinea pigs, mini pigs, hamsters, and pet birds such as parrots.

In an aspect, the effective amount of IL-10 peptide or the isolated antibody that specifically binds an interleukin-10 peptide reduces egg shedding in the companion animal. In another aspect, the effective amount of the IL-10 peptide or isolated antibody that specifically binds an interleukin-10 peptide reduces reinfection by parasitic worms in the companion animal. In another aspect, the effective amount of IL-10 peptide or isolated antibody that specifically binds and interleukin-10 peptide results in the natural development of immunity to the parasitic worm such that on an exposure 2 weeks or later results in the prevention of infection. Without being held to theory, it is believed that the parasitic worms downregulate immunity by stimulating the host to release IL-10, however, when IL-10 is blocked, the immune system is not down-regulated, allowing for natural immunity to develop such that the animal resists reinfection. Effective amount of the interleukin-10 peptide or the isolated antibody that specifically binds an interleukin-10 peptide for the treatment of companion animals are 3 g/kg feed to 0.001 mg/Kg feed, specifically 1 g/Kg feed to 0.341 g/Kg feed.

In one aspect, the IL-10 peptide or the isolated antibody that specifically binds an interleukin-10 peptide is administered to the animal when the animal is infected with parasitic worms. Without being held to theory, it is believed that administering to an animal that has been exposed to a parasitic worm allows for natural immunity and thus the animal will become naturally resistant. In one aspect, the IL-10 peptide or the isolated antibody that specifically binds an interleukin-10 peptide administered daily for 2 weeks or less. In one aspect, the IL-10 peptide or the isolated antibody that specifically binds an interleukin-10 peptide is administered for 7-10 days. In another aspect, the IL-10 peptide or the isolated antibody that specifically binds an interleukin-10 peptide is administered at a high dose for 3-5 days. In another aspect, the isolated antibody that specifically binds an interleukin-10 peptide is administered daily until the animal is no longer infected with parasitic worm.

In yet another aspect, the methods include controlling parasitic worms having a lifecycle stage that includes the gastrointestinal tract of a human subject, comprising orally administering to the human subject an effective amount of an interleukin-10 peptide or an isolated antibody that specifically binds an interleukin-10 peptide. In one aspect, the human subject resides in a region where helminthiasis is prevalent, such as third world country. In the case of a human subject, the effective amount of an interleukin-10 peptide or an isolated antibody that specifically binds an interleukin-10 peptide can be administered in the form of a pharmaceutical composition comprising a pharmaceutically acceptable excipient. Pharmaceutically acceptable excipients are well-known in the art and include diluents, fillers, binders, lubricants, as well as release-controlling excipients such as sustained-release polymers. Pharmaceutical compositions include oral compositions such as tablets, capsules and liquid compositions.

As used herein, the term "peptide" includes the peptide as well as pharmaceutically acceptable salts of the peptide. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids.

As used herein, the term "antibody", or "immunoglobulin", encompasses naturally occurring antibodies, such as polyclonal and monoclonal antibodies, as well as artificial or synthetic antibodies or genetically engineered forms of antibodies, including single chain (domain) antibodies (e.g., camelid antibodies, chimeric, and bifunctional antibodies, as well as fragments thereof.

The term "isolated antibody" as used herein, refers to an antibody that is at least partially purified from other naturally associated molecules, or substantially free of antibodies having different antigenic specificities. In some cases, particularly in the case of egg yolk antibodies, the antibody may comprise 50-70% or more of an isolated antibody preparation.

An IL-10 peptide of the present disclosure includes the amino acid sequences of SEQ ID NO: 1, SEQ ID NO: 2, SEQ ID NO: 3, SEQ ID NO: 4, SEQ ID NO. 5, SEQ ID NO: 6, SEQ ID NO: 7, SEQ ID NO: 8, SEQ ID NO. 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO. 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and combinations thereof (see Table 1). In particularly suitable embodiments, the IL-10 peptide has an amino acid sequence of SEQ ID NO: 9.

TABLE 1

Sequence ID NO. and Corresponding Amino Acid Sequence.

| SEQ ID NO. | AMINO ACID SEQUENCE | Organism |
|---|---|---|
| SEQ ID NO. 1 | DDELNIQL | Chicken, quail, turkey |
| SEQ ID NO. 2 | VLPRAMQT | chicken |
| SEQ ID NO. 3 | VLPRAMKT | Quail and turkey |
| SEQ ID NO. 4 | EKMDENGI | Chicken, quail, turkey |
| SEQ ID NO. 5 | EPTCLHFS | Chicken, quail, turkey |
| SEQ ID NO. 6 | DQMGDLL | pig |
| SEQ ID NO. 7 | DQLHSLL | cow |
| SEQ ID NO. 8 | VMPKAESD | pig |
| SEQ ID NO. 9 | VMPQAENH | Cow/sheep |
| SEQ ID NO. 10 | SKLQERGV | pig |
| SEQ ID NO. 11 | SELQERGV | cow |
| SEQ ID NO. 12 | ENSCIHFP | pig |
| SEQ ID NO. 13 | DSSCIHLP | cow |
| SEQ ID NO. 14 | DQLNSML | sheep |
| SEQ ID NO. 15 | NMLQERGV | sheep |

TABLE 1-continued

Sequence ID NO. and Corresponding Amino Acid Sequence.

| SEQ ID NO. | AMINO ACID SEQUENCE | Organism |
|---|---|---|
| SEQ ID NO. 16 | DSSCTHFP | sheep |
| SEQ ID NO. 17 | DQLDNMLL | horse |
| SEQ ID NO. 18 | VMPQAENH | horse |
| SEQ ID NO. 19 | SKLQEKGV | horse |
| SEQ ID NO. 20 | ENSCTHFP | horse |
| SEQ ID NO. 21 | DDLEIGL | fish |
| SEQ ID NO. 22 | VLPTAIADMTEE | fish |
| SEQ ID NO. 23 | TQMEGKGP | fish |
| SEQ ID NO. 24 | NQCCRFV | fish |
| SEQ ID NO. 25 | DKLDNILL | Dog, Canis lupis familiaris |
| SEQ ID NO. 26 | VMPRAEN | dog |
| SEQ ID NO. 27 | SKLQEKGV | dog |
| SEQ ID NO. 28 | EDDCTHFP | dog |
| SEQ ID NO. 29 | DELHSILL | Cat, Felis catus |
| SEQ ID NO. 30 | VMPQAENE | cat |
| SEQ ID NO. 31 | SKLQEKGV | cat |
| SEQ ID NO. 32 | EDNCTHFS | cat |
| SEQ ID NO. 33 | DQLNSMLL | rabbit |
| SEQ ID NO. 34 | VMPQAENH | rabbit |
| SEQ ID NO. 35 | SKLQEEGV | rabbit |
| SEQ ID NO. 36 | ENSCIHFP | rabbit |
| SEQ ID NO. 37 | DQLDNVLL | guinea pig |
| SEQ ID NO. 38 | VMPQAEKH | guinea pig |
| SEQ ID NO. 39 | NKLQDQGV | guinea pig |
| SEQ ID NO. 40 | EDSCAHFP | guinea pig |

SEQ ID NOs: 6-20 are amino acid sequences corresponding to peptides of the IL-10 cytokine in herbivorous mammals.

The present disclosure further includes antibodies that specifically bind to the IL-10 peptides (also referred to herein as "anti-IL-10 antibody"). These antibodies have surprisingly been found to improve cattle performance after exposure to helminths, for example. The antibodies of the present disclosure specifically bind to IL-10 peptides including the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, SEQ ID NO: 15, SEQ ID NO: 16, SEQ ID NO: 17, SEQ ID NO: 18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and combinations thereof. In some embodiments, the isolated antibodies specifically bind to IL-10 peptides having an amino acid sequence of SEQ ID NOs: 6-20. In other embodiments, the isolated antibodies bind SEQ ID NO: 9.

The present disclosure is further directed to generating antibodies that specifically bind to the IL-10 peptides. In one embodiment, an antibody is generated by administering the IL-10 peptides described above to an animal. Suitable animals to administer the IL-10 peptides for generating the antibodies include, for example, poultry. Exemplary poultry include chickens, turkeys, ducks, quail, and pheasant. Specific poultry include turkeys and chickens. Additional animals include livestock animals such as cattle, pigs, sheep, and fish.

Exemplary methods for administering the IL-10 peptides to the animal include injection and oral administration. Injection and oral administration optionally include use of an adjuvant such as, for example, Freund's Complete adjuvant and Cholera toxin. Administration optionally further includes conjugation of the IL-10 peptide to a carrier protein such as, for example, bovine gamma globulin or keyhole limpet hemocyanin.

In one embodiment, antibodies to the IL-10 peptides are generated by an animal (referred to herein as the "producer animal"). When the animal is an avian animal, as known by those skilled in the art, the antibodies generated are passed to the egg, and may specifically be concentrated in the egg yolk of the avian producer animal. Alternatively, antibodies of the present disclosure may be isolated from the animal itself such as from serum.

In one embodiment, the antibody is an avian egg yolk antibody. Egg yolks derived from a laying hen are inexpensive, convenient and can be safer to handle as compared to the hyperimmunized mammalian sera. Also, egg yolk antibodies are able to stand up to the scrutiny under modern animal protection regulations. Immunoglobulin Y (IgY) is an avian immunoglobulin.

To produce avian egg yolk antibodies, the IL-10 peptides are injected into laying fowl, such as hens, preferably at various intervals, to induce an immune response. The hens may be injected intramuscularly or sub-cutaneously. The specific mode of injection is not essential. It is well known that the IgY antibodies produced by the hens in response to such an immune challenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying methods, and the resulting dried powder may be encapsulated or otherwise used in oral dosage forms.

Alternatively, a procedure of partial purification or fractionation may be carried out to remove the majority of the non-aqueous bio-molecules and granules and optionally the majority of other proteins in the egg yolk. Exemplary purification techniques include the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, pH is about 5-7. Desirably, the temperature in this step is within about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include, but are not limited to, $NaCl$, $Na_2SO_4$, $(NH_4)_2SO_4$, $KCl$, $CaCl_2$, and $MgSO_4$. Specific salts include $Na_2SO_4$ and $(NH_4)_2SO_4$. The salt concentration for precipitating antibodies depends on the type of the salt. In one embodiment, the salt is present in an amount of higher than 15% and lower than 35% by weight, specifically between 20% and 30% by weight of the salt, on the basis of the final volume of the yolk supernatant.

Alternatively, the antibodies may be purified or isolated using any conventional technique such as by immunoaffinity purification.

In one embodiment, egg yolk antibodies are prepared by the following method. Laying hens are inoculated with IL-10 peptide. Optionally, an adjuvant is administered in conjunction with the IL-10 peptide to enhance the immunization. An adjuvant useful for this purpose is a water-in-oil emulsion adjuvant such as complete Freund's adjuvant. The IL-10 peptide causes the hens to produce anti-IL-10 antibodies which are passively transferred into the egg yolk of eggs laid by the hens.

Egg yolks or whole eggs containing the anti-IL-10 antibody can be collected and homogenized to form an emulsion. The resulting emulsion can be dried to form a powder containing the anti-IL-10 antibody. This powder can then be formulated in a manner appropriate to the administration route and then administered to the desired animals using methods known in the art. The preparation is preferably administered orally, such as in an oral dosage form or in a supplement to the animal's diet.

The antibodies that specifically bind to IL-10 peptides may be isolated and purified from animal serum or egg using a suitable method known in the art. Such methods include affinity chromatography, as well as other suitable methods for antibody isolation and purification known in the art and described in U.S. Pat. No. 6,608,172 and De Meulenaer et al., "Isolation and Purification of Chicken Egg Yolk Immunoglobulins: A Review," Food and Agricultural Immunology, Vol. 13(4), 2001, hereby incorporated by reference to the extent that they are consistent herewith. In one particularly suitable embodiment, the production animal is an avian animal such as a chicken, turkey, duck, or quail, and the antibody is isolated from the egg yolk of the egg of the avian animal.

In one embodiment, the egg yolk or serum including the antibodies are further dried to form a powder including the antibodies. The whole egg, egg yolk or parts of the egg may be spray dried. Serum may be separated from whole blood according to methods known by those skilled in the art. Spray drying of egg and serum may be performed using known spray drying methods and commercially available spray drying equipment. Dry egg and serum powders may also be prepared by lyophilization. The dried egg, egg yolk or serum powder may then be introduced into animal feeds as a feed additive to transfer antibodies to an animal.

In another aspect, isolated antibodies can include antibodies in serum, or antibodies that have been purified to varying degrees. Such antibodies may include polyclonal antibodies, camelid antibodies, monoclonal antibodies, humanized or chimeric antibodies, anti-idiotypic antibodies, single chain antibodies, Fab fragments, fragments produced from a Fab expression library, epitope-binding fragments of the above, and the like. Production of antibodies is well-known in the art.

In yet another aspect, an antibody is isolated from the colostrum of an animal such as from bovine colostrum.

The methods disclosed herein can be achieved using animal feed additives including the IL-10 peptides, or isolated antibodies which specifically bind to IL-10 peptides.

As used herein, the term "feed" broadly refers to a material, liquid or solid, that is used for nourishing an animal, and for sustaining normal or accelerated growth of an animal including newborns or young and developing animals. The term includes a compound, preparation, mixture, or composition suitable for intake by an animal. Specifically, the feed is suitable for herbivorous mammals such as cattle, horses, sheep and goats; for fish; or for companion animals. A feed composition comprises a basal food composition and one or more feed additives. The term "basal food composition" refers to a food composition combinable with additives such as the peptides and antibodies described herein. Basal animal food compositions may include components such as proteins, grains, flavor compositions, vitamins, minerals, preservatives, and the like. Basal food compositions can be suitable for ingestion by a target animal. The term "feed additive" as used herein refers to components included in small quantities for the purpose of fortifying basic feed with nutrients, stimulants, medicine, or to promote feed intake or alter metabolism. Feed additives include pre-mixes of biological compositions, or in the present disclosure, pre-mixes of IL-10 peptide or isolated antibody that specifically binds to IL-10 peptide.

In one embodiment, the methods disclosed herein are achieved using animal feed additive including IL-10 peptides including the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. Particularly, the feed additive may include IL-10 peptides having an amino acid sequence of SEQ ID NOs: 6-20.

In another embodiment, the methods of the present disclosure utilize an animal feed additive including isolated antibodies that specifically bind to the IL-10 peptide including the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In particularly suitable embodiments, the feed additive includes isolated antibodies that specifically bind to IL-10 peptides having the amino acid sequence of SEQ ID NOs: 6-20.

The IL-10 peptides or isolated antibodies which specifically bind to IL-10 peptides may be added to an animal feed as a feed additive or mixed into an animal feed by a method known in the art for mixing feed additives and animal feed. In one embodiment, the IL-10 peptide or isolated antibody which specifically binds to the IL-10 peptide is directly added to the animal feed or mixed with the animal feed just prior to feeding the animal. In another embodiment, since feeds may be pelleted or extruded, the IL-10 peptide or isolated antibody which specifically binds to the IL-10 peptide may be coated on the surface of feed (pellet) after the feed has been pelleted or extruded (post pelleted application) in order to maintain functional properties of the IL-10 peptide or isolated antibody which specifically binds to the IL-10 peptide. The addition of the IL-10 peptide or isolated antibody which specifically binds to the IL-10 peptide post pelleting can be aided by mixing the IL-10 peptide or isolated antibody which specifically binds to the IL-10 peptide in water, oil, or another suitable carrier and spraying it on the pellets as they exit the pellet die.

The amount of the IL-10 peptide or isolated antibody that specifically binds to IL-10 peptide added and/or mixed with the animal feed depends on the feeding regimen and the type of feed for the animal, and may be determined by those skilled in the art. Typically, the amounts of IL-10 peptides and/or isolated antibodies to IL-10 peptide to be used in an animal feed are summarized in Table 2 below. Antibody prepared using other sources may be calculated as equivalents using Table 2.

TABLE 2

Dose of Anti-IL-10 Antibody in Animal Feed (mg/Kg diet) prepared using egg yolk antibody.

| Source | Low Dose | High Dose |
| --- | --- | --- |
| Affinity purified anti-peptide | 0.0015 | 0.5 |
| Anti-peptide IgY | 0.015 | 50 |
| Dry Immune Yolk | 0.8 | 4000 |
| Dried Immune Whole Egg | 1.5 | 7500 |

The doses shown are based on the amount of epitope specific antibody in total IgY (1 to 10%), the amount of IgY in egg (5-10 mg/Kg of feed), antibody losses due to drying storage and gastrointestinal degradation.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

Specifically, the animal feed including the feed additive of either IL-10 peptide or isolated anti-IL-10 antibody is a feed for an herbivorous mammal such as a cow, horse, goat or sheep.

The methods of the present disclosure are generally directed to methods for treating infections caused by parasitic worms having a lifecycle stage that includes the gastrointestinal tract in an animal, or in an animal with a status of convalescence carriers of pathogen. In one embodiment, the methods involve injecting or orally administering an IL-10 peptide to an animal, thereby producing antibodies within the animal that specifically bind to the IL-10 peptide. IL-10 cytokine production is associated with down regulation of inflammation, and the IL-10 cytokine functions as an essential immunoregulator of the intestinal tract. The antibody to IL-10 peptide prevents the IL-10 cytokine from down regulating the immune system, thereby allowing the immune system to eliminate the pathogen.

In some embodiments, the methods involve injecting or orally administering an antibody to the IL-10 peptide to an animal. The term "animal", as used herein to describe animals administered an IL-10 peptide or isolated antibody to the IL-10 peptide in accordance with the present disclosure.

The invention is further illustrated by the following non-limiting examples.

EXAMPLES

Example 1: Anti-IL-10 Antibody Production

In this Example, the concentration of anti-IL-10 antibody production contained within the egg yolk of IL-10 peptide-administered producer hens was determined by using Enzyme-linked immunosorbent assay (ELISA) techniques.

Specifically, each of IL-10 peptide SEQ ID NO: 9 was conjugated to hen ovalbumin (OVA, Sigma, St. Louis, Mo.) for ELISA using glutaraldehyde procedure. A 96-well NUNC® immunosorbent F-series microplate (Sigma, St. Louis, Mo.) was coated with 100 µg/plate of peptide-specific OVA conjugate in sodium carbonate coating buffer having a pH of 9.6. The plate was allowed to coat overnight (100 µl/well) at 4° C. Dry egg yolk samples containing antibody to IL-10 Peptide SEQ ID NO. 9 were diluted 1:10 in acidic PBS having a pH of 4 and allowed to incubate overnight at 4° C. After overnight incubation, the antibody was extracted using centrifugation and used as a source of antibody to determine specificity for the peptide conjugated to the IL-10 peptide. The plate coated with OVA-peptide conjugate was washed 6 times with PBS/0.5% TWEEN® (polysorbate 20, polyoxyethylene (20) sorbitan monolaurate) solution, blocked with non-protein blocking buffer (200 µl/well, Pierce Scientific, Rockford, Ill.), and allowed to incubate at room temperature for at least 1 hour. The plate was washed 6 times and then samples of either adjuvant only injected control or egg antibody (isolated as described above) were added at a concentration of 100 µl/well in duplicate at 10× serial dilutions starting at 1:20. Primary antibodies were incubated for 1 hour, the plate was washed 6 times, and then secondary antibody (HRP-conjugated goat anti-chicken antibody, Bethyl Labs, Montgomery, Tex.) was diluted in blocking buffer 1:5000 and added at a concentration of 100 µl/well. Secondary antibody was incubated for 30 minutes, the plate was washed 6 times, and then substrate solution containing 19.74 ml 0.05M sodium acetate, 100 µl 20 mg/mL 3,3',5,5' Tetramethyl Benzidine (TMB), 128 µl 0.5M $H_2O_2$ was added at a concentration of 125 µl/well and allowed to incubate until sufficient color development during the linear phase of development (blue color indicates primary antibody presence). A stop solution (0.5M sulfuric acid) was added to produce a yellow stable color and the plate was read at 450 nm on a BIOTEK® EL800 plate reader. Triplicate optical densities were averaged and blocking buffer background was subtracted to produce a final optical density. The optical density of antibody to IL-10 peptide SEQ ID NO. 9 and FCA control were compared to determine specificity and dose level used in the final chick experiment (see Table 3).

TABLE 3

Antibody titer for cow anti-IL-10 antibody. Antibody extracts from control eggs and eggs from hens injected with an IL-10 peptide conjugate were serially diluted and added to plate bound peptide and analyzed as described above. The antibody to the IL-10 antibody could be diluted up to 1:320 (titer) before the absorbance equaled background absorbance.

| Dilution | Cow Anti-IL-10 | Control Antibody |
|---|---|---|
| 1:20 | 2.114 | 1.298333333 |
| 1:40 | 1.791 | 1.141333333 |
| 1:80 | 1.308 | 0.932666667 |
| 1:160 | 0.905666667 | 0.737333333 |
| 1:320 | 0.720666667 | 0.553666667 |
| 1:640 | 0.375 | 0.409666667 |
| 1:1280 | 0.254333333 | 0.294666667 |

Example 2: Calf Growth after an Established Parasite Infection when Treated with Anti-IL-10 Antibody (aIL-10)

The objective was to use the monoclonal egg yolk antibody (MCA) designed to bind bovine IL-10 (Example 1), and induce long term protection against common internal grazing parasites and increase animal weight gain.

Figure 2:
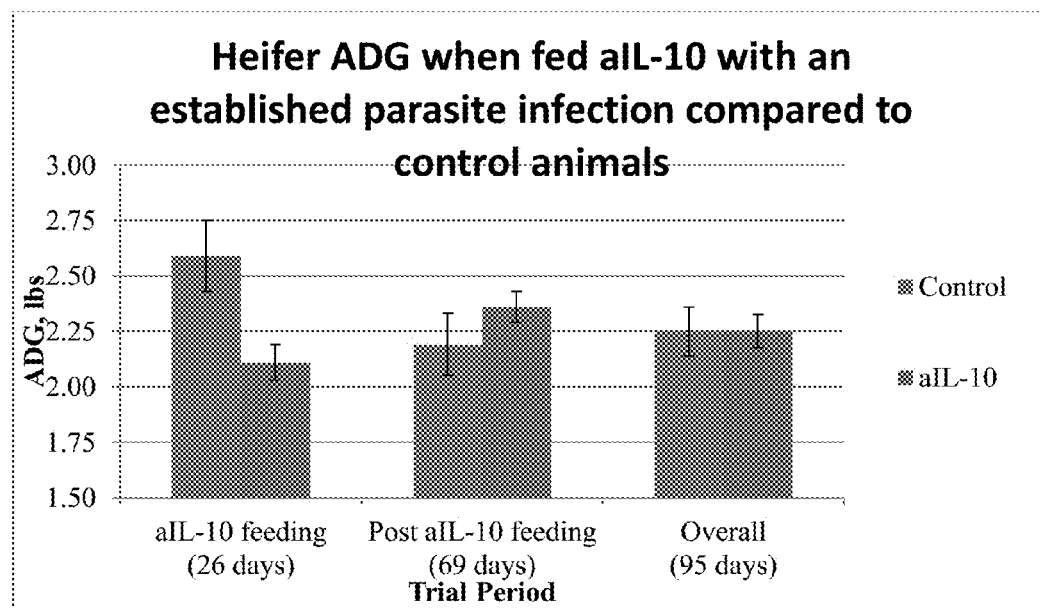
FIG. 2 shows the average daily growth of calves with an established parasite infection comparing control animals to animals fed anti-IL-10 antibody.

Eight animals were studied. The 4 control animals were non-dewormed. The 4 treated animals were fed aIL-10 at approximately 26 mg of anti-IL10 peptide specific antibody (or 14 g dried egg yolk/head/day). The protocol was as follows:

Dose all calves with 7,700 *Haemonchus* infective larvae
Determine fecal egg counts (FEC), once calves are shedding eggs, start feeding aIL-10 to respective animals
Allow all animals free choice consumption of haylage Feed all animals 4 lbs/day of a common calf grain supplement
  Within the 4 lbs of calf starter, 26 mg of IL-10 peptide specific antibody or 14 g dried egg yolk will be the carrier for the aIL-10 treatment
Removed aIL-10 from feed after 26 days
Re-infected all calves with 6,000 *Haemonchus* 23 days after stopped aIL-10 feeding
Weigh animals weekly—ADG=average daily weight gain The timeline of treatment is given in FIG. 1. FIG. 2 shows the average daily growth of the calves comparing control with no antibody treatment to calves fed anti-IL-10 antibody. During the aIL-10 feeding period, animals fed the aIL-10 egg yolk had a lower growth rate than control animals. This suggests the aIL-10 acted as an immune stimulant. Further determination of "ideal" dosage level, and duration needs to be considered for which no growth suppression is detected when feeding aIL-10. Despite a short term 19% growth reduction, animals fed aIL-10 and then re-exposed to *Haemonchus* out performed control animals by 10%, which resulted in similar overall animal performance. These data support that cattle fed aIL-10 during their first exposure to *Haemonchus* developed resistance, likely through an immune mediated pathway, during subsequent exposure, where as cattle exposed to *Haemonchus* in the absence of aIL-10, did not have resistance and succumbed to the reinfection as shown by weight performance.

Figure 3:
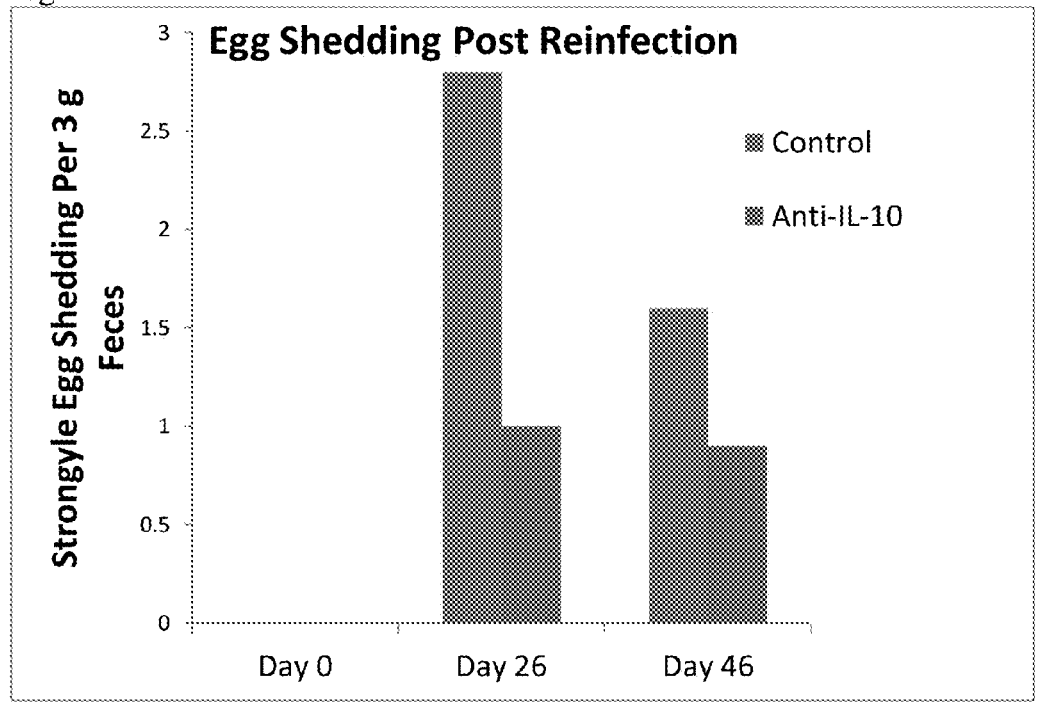
FIG. 3 shows the egg shedding post reinfection for control animals versus animals fed anti-IL-10 antibody.

As shown in FIG. 3, treatment with anti-IL-10 antibody also reduced egg shedding in the animals treated with anti-IL-10 antibody. These data also support a general immune resistance during re-exposure if animal were fed aIL-10 during their first exposure.

Example 3: Field Trial of Anti-IL-10 Antibody in Growing Dairy Calves

The objective of this trial is to verify that the anti-IL-10 antibody induces long term protection against common internal grazing parasites and increases animal weight gain in growing dairy calves.

100 animals will be grouped as follows:
Negative Control (non-dewormed)
Positive Control (10 mg-acting dewormer)
MCA 1, (feed MCA 14 days, at 14 g/hd/d)
MCA 2, (feed MCA 14 days, at 7 g/hd/d)
MCA 3, (feed MCA 14 days, at 3.5 g/hd/d)
20 animals per treatment
MCA=anti-IL-10 antibody
The animals will be treated as follows:
Turn all 100 calves out on pasture for approximately 28 days—this will allow for a natural infection of all calves
After approximately 28 days on pasture, fecal sample for parasite egg levels, weigh, deworm positive control, and assign to treatment by weight
Once sorted into treatment groups, maintain in 5 separate pastures where forage is not limited for 14 days
Feed all animals 5 lbs supplement/hd/d
Feed is used to carry the MCA levels of 1, 2, and 3
Allows all groups to be exposed to similar pastures
After 14 days (feeding/treatment period), weigh and fecal sample
Comingle all animals and maintain as one group until the end of the season
Weigh every 28 days and fecal sample

Example 4: Field Trial of Anti-IL-10 Antibody in Grazing Lambs

The objective of this trial is to verify that the anti-IL-10 antibody induces long term protection against common internal grazing parasites and increases animal weight gain in grazing lambs.

100 animals will be grouped as follows:
Negative Control (non-dewormed)
Positive control (de-wormed per industry recommendations)
MCA 1, [feed MCA 14 days, at 2.3 g/hd/d, (similar as 14 g/hd/d bovine)]
MCA 2, (feed MCA 14 days, at 1.15 g/hd/d)
MCA 3, (feed MCA 14 days, at 0.58 g/hd/d)
20 animals per treatment
The animals will be treated as follows:
Turn all 100 lambs out on pasture for approximately 21 days. This will allow for a natural infection of all lambs.
After approximately 21 days on pasture, fecal for EPG, weigh, deworm positive control, and assign to treatment groups.
Once sorted into treatment groups, maintain each treatment in separate pens. Feed all animals ad lib haylage and 1.0 lbs supplement/hd/d.
After 14 days (supplement period) weigh and fecal sample. Comingle all animals and maintain as one group until end of season.
Weigh every 28 days and fecal sample.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of controlling parasitic worms having a lifecycle stage that includes the gastrointestinal tract of a herbivorous mammal, comprising
orally administering to the herbivorous mammal an effective amount of an isolated antibody that specifically binds an interleukin-10 peptide when orally administered to the herbivorous mammal,
wherein the interleukin-10 peptide is SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO:20, and wherein the mammal is infected with or suspected of being infected with a parasitic worm having a lifecycle stage that includes the gastrointestinal tract of the herbivorous mammal.

2. The method of claim 1, wherein the isolated antibody that specifically binds the interleukin-10 peptide is an egg yolk antibody.

3. The method of claim 1, wherein the isolated antibody that specifically binds the interleukin-10 peptide is administered in a feed composition.

4. The method of claim 1, wherein the herbivorous mammal is a bovine, an equine, an ovine, a caprine, a goat, a llama, an alpaca, a deer, an elk, or a pig.

5. The method of claim 1, wherein the herbivorous mammal is a ruminant or pre-ruminant animal.

6. The method of claim 5, wherein the ruminant or pre-ruminant animal is a bovine, and the parasitic worm is a *Haemonchus* species.

7. The method of claim 1, wherein the effective amount of the isolated antibody that specifically binds an interleukin-10 peptide increases weight gain in the herbivorous mammal.

8. The method of claim 1, wherein the effective amount of the isolated antibody that specifically binds an interleukin-10 peptide reduces egg shedding in the herbivorous mammal.

9. The method of claim 8, wherein the effective amount of the isolated antibody that specifically binds an interleukin-10 peptide reduces reinfection by parasitic worms in the herbivorous mammal.

10. The method of claim 1, wherein the herbivorous mammal is part of a population of mammals that are infected with parasitic worms that are resistant to one or more antihelminthic agents.

11. The method of claim 10, wherein the antihelminthic agent is a benzimidizole, a hydropyrimidine, an imidazothiazole, or a macrocylic lactone.

12. The method of claim 1, wherein administering the effective amount of the isolated antibody that specifically binds the interleukin-10 peptide decreases the likelihood of death of the mammal.

13. The method of claim 1, wherein the isolated antibody that specifically binds the interleukin-10 peptide is orally administered daily for 2 weeks or less.

14. The method of claim 13, wherein administration of the isolated antibody that specifically binds the interleukin-10 peptide is not resumed for at least 2 weeks after daily administration is ceased.

15. A method of increasing weight gain or increasing feed efficiency in a herbivorous mammal, comprising orally administering to the herbivorous mammal an effective amount of an isolated antibody that specifically binds an interleukin-10 peptide when orally administered to the herbivorous mammal, wherein the herbivorous mammal is infected with or is suspected of being infected with a parasitic worm having a lifecycle stage that includes the gastrointestinal tract of the herbivorous mammal, wherein the IL-10 peptide is SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

16. The method of claim 15, wherein the isolated antibody that specifically binds the interleukin-10 peptide is an egg yolk antibody.

17. The method of claim 15, wherein the isolated antibody that specifically binds the interleukin-10 peptide is administered in a feed composition.

18. The method of claim 15, wherein the herbivorous mammal is a bovine, a horse, a sheep, a goat, a llama, an alpaca, a deer, an elk, or a pig.

19. The method of claim 15, wherein the herbivorous mammal is a ruminant or pre-ruminant animal.

20. The method of claim 19, wherein the ruminant or pre-ruminant animal is a bovine, and the pirasitic worm is a *Haemonchus* species.

21. The method of claim 15, wherein the effective amount of the isolated antibody that specifically binds an interleukin-10 peptide reduces egg shedding in the herbivorous mammal.

22. The method of claim 15, wherein the effective amount of the isolated antibody that specifically binds an interleukin-10 peptide reduces reinfection by parasitic worms in the herbivorous mammal.

23. The method of claim 15, wherein the herbivorous mammal is part of a population of mammals that are infected with parasitic worms that are resistant to one or more antihelminthic agents.

24. The method of claim 23, wherein the antihelminthic agent is a benzimidizole, a hydropyrimidine, an imidazothiazole, or a macrocylic lactone.

25. The method of claim 15, wherein administering the effective amount of the isolated antibody that specifically binds the interleukin-10 peptide decreases the likelihood of death of the mammal.

26. The method of claim 15, wherein the isolated antibody that specifically binds the interleukin-10 peptide is orally administered daily for 2 weeks or less.

27. The method of claim 26, wherein administration of the isolated antibody that specifically binds the interleukin-10 peptide is not resumed for at least 2 weeks after daily administration is ceased.

28. A method of providing resistance to reinfection with a parasitic worm having lifecycle stage that includes the gastrointestinal tract of an herbivorous mammal, comprising orally administering to the herbivorous mammal an effective amount of an isolated antibody that specifically binds an interleukin-10 peptide when orally administered to the herbivorous mammal, wherein the herbivorous mammal was infected with the parasitic worm at the time of oral administration of the isolated antibody that specifically binds the interleukin-10 peptide, and wherein the IL-10 peptide is SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

29. The method of claim 28, wherein the isolated antibody that specifically binds the interleukin-10 peptide is an egg yolk antibody.

30. The method of claim 28, wherein the isolated antibody that specifically binds the interleukin-10 peptide is administered in a feed composition.

31. The method of claim 28, wherein the herbivorous mammal is a bovine, an equine, an ovine, a caprine, a goat, a llama, an alpaca, a deer, an elk, or a pig.

32. The method of claim 28, wherein the herbivorous mammal is a ruminant or pre-ruminant animal.

33. The method of claim 32, wherein the ruminant or pre-ruminant animal is a bovine, and the parasitic worm is a *Haemonchus* species.

34. The method of claim 28, wherein the effective amount of the isolated antibody that specifically binds an interleukin-10 peptide increases weight gain in the herbivorous mammal.

35. The method of claim 28, wherein the effective amount of the isolated antibody that specifically binds an interleukin-10 peptide reduces egg shedding in the herbivorous mammal.

36. The method of claim 28, wherein herbivorous mammal is part of a population of mammals that are infected with parasitic worms that are resistant to one or more antihelminthic agents.

37. The method of claim 36, wherein the antihelminthic agent is a benzimidizole, a hydropyrimidine, an imidazothiazole, or a macrocylic lactone.

38. The method of claim 28, wherein administering the effective amount of the isolated antibody that specifically binds the interleukin-10 peptide decreases the likelihood of death of the mammal.

39. The method of claim 28, wherein the isolated antibody that specifically binds the interleukin-10 peptide is orally administered daily for 2 weeks or less.

40. The method of claim 39, wherein administration of the isolated antibody that specifically binds the interleukin-10 peptide is not resumed for at least 2 weeks after daily administration is ceased.

* * * * *